US005464966A

United States Patent [19]
Gaitan et al.

[11] Patent Number: 5,464,966
[45] Date of Patent: Nov. 7, 1995

[54] MICRO-HOTPLATE DEVICES AND METHODS FOR THEIR FABRICATION

[75] Inventors: Michael Gaitan, Gaithersburg; John S. Suehle, Westminister; Stephen Semancik, Mt. Airy; Richard E. Cavicchi, Washington Grove, all of Md.

[73] Assignee: The United States of America as represented by the Secretary of Commerce, Washington, D.C.

[21] Appl. No.: 965,947

[22] Filed: Oct. 26, 1992

[51] Int. Cl.⁶ .............................. H05B 3/00; G01F 1/68; H01C 1/012
[52] U.S. Cl. .......................... 219/544; 219/543; 338/307; 437/918; 73/204.26
[58] Field of Search .................... 219/553, 543, 219/544, 548, 549, 505; 338/306–309, 292, 300, 262, 211, 34; 118/725; 437/918, 966, 228, 225, 245; 29/611, 620, 610.1; 73/204.26, 31.05, 31.06; 422/98

[56] References Cited

U.S. PATENT DOCUMENTS

| | | |
|---|---|---|
| 3,509,431 | 4/1970 | Iles et al. . |
| 3,571,917 | 3/1971 | Merryman et al. . |
| 3,961,155 | 6/1976 | Weldon et al. .......................... 219/543 |
| 4,076,061 | 11/1977 | Johnson ..................................... 338/34 |
| 4,103,073 | 7/1978 | McAlear et al. . |
| 4,142,925 | 3/1979 | King et al. . |
| 4,181,544 | 1/1980 | Cho . |
| 4,286,377 | 9/1981 | Hurko et al. . |
| 4,292,730 | 10/1981 | Ports . |
| 4,425,379 | 1/1984 | Vora et al. . |
| 4,470,875 | 9/1984 | Poteat . |
| 4,501,144 | 2/1985 | Higashi et al. ..................... 73/204.26 |
| 4,574,264 | 3/1986 | Takahashi et al. . |

(List continued on next page.)

FOREIGN PATENT DOCUMENTS 0285833 10/1988 European Pat. Off. .
0376721 7/1990 European Pat. Off. .
3743398 7/1989 Germany ................................. 338/34

OTHER PUBLICATIONS

M. Parameswaran et al, "A New Approach for the Fabrication of Micromachined Structures", *Sensors and Actuators*, vol. 19 (1989), pp. 289–307.

M. Parameswaran et al, "Micromachined thermal Radiation Emitter from a Commercial CMOS Process", *IEEE Electron Device Letters*, vol. 12, No. 2 (1991), pp. 57–60.

Wang et al "A microfabricated Array of Multiple Thin Film Metal Oxide Sensors for Multicomponent Gas and Vapor Quantification", *Proceedings from the IEEE Solid State Sensors and Actuators Workshop*, Hilton Head S.C. (1992) p. 23.

Najafi et al "An Integrated Multi–Element Ultra–Thin–Film Gas Analyzer", *Proceedings from the IEEE Solid State Sensors and Actuators Workshop*, Hilton Head, S.C. (1992), p. 19.

(List continued on next page.)

Primary Examiner—John A. Jeffery
Attorney, Agent, or Firm—Lowe, Price, LeBlanc & Becker

[57] ABSTRACT

A design and fabrication methodology, for silicon micromachined micro-hotplates which are manufactured using commercial CMOS foundries techniques with additional post-fabrication processing. The micro-hotplates are adaptable for a host of applications. The methodology for the fabrication of the micro-hotplates is based on commercial CMOS compatible micromachining techniques. The novel aspects of the micro-hotplates are in the design, choice and layout of the materials layers, and the applications for the devices. The micro-hotplates have advantages over other similar devices in the manufacture by a standard CMOS process which include low-cost and easy integration of VLSI circuits for drive, communication, and control. The micro-hotplates can be easily incorporated into arrays of micro-hotplates each with individualized circuits for control and sensing for independent operation.

31 Claims, 7 Drawing Sheets

U.S. PATENT DOCUMENTS

| | | | |
|---|---|---|---|
| 4,587,105 | 5/1986 | Bonne et al. | 422/98 |
| 4,595,485 | 6/1986 | Takahashi et al. | 204/406 |
| 4,612,083 | 9/1986 | Yasumoto et al. . | |
| 4,682,503 | 7/1987 | Higashi et al. | 73/204.26 |
| 4,696,188 | 9/1987 | Higashi | 338/308 |
| 4,703,555 | 11/1987 | Hubner | 338/34 |
| 4,706,493 | 11/1987 | Chang et al. | 73/204.26 |
| 4,728,591 | 3/1988 | Clark et al. . | |
| 4,740,387 | 4/1988 | Manaka | 437/141 |
| 4,743,954 | 5/1988 | Brown . | |
| 4,784,721 | 11/1988 | Holmen et al. | 338/42 |
| 4,808,967 | 2/1989 | Rice et al. | 338/309 |
| 4,824,803 | 4/1989 | Us et al. . | |
| 4,878,770 | 11/1989 | Ruggierio et al. | 338/308 |
| 4,895,616 | 1/1990 | Higashi et al. | 156/647 |
| 4,897,361 | 1/1990 | Harriott et al. . | |
| 4,897,814 | 1/1990 | Clark . | |
| 4,912,975 | 4/1990 | Ohta et al. | 73/204.26 |
| 4,918,032 | 4/1990 | Jain et al. | 437/228 |
| 4,985,373 | 1/1991 | Levinstein et al. . | |
| 5,019,885 | 5/1991 | Yagawara et al. | 338/34 |
| 5,050,091 | 9/1991 | Rubin . | |
| 5,050,429 | 9/1991 | Nishimoto et al. | 73/204.26 |
| 5,071,770 | 12/1991 | Kolesar, Jr. . | |
| 5,075,250 | 12/1991 | Hawkins et al. . | |
| 5,111,179 | 5/1992 | Flassayer et al. | 338/308 |
| 5,131,954 | 7/1992 | Vogeli et al. . | |
| 5,310,449 | 5/1984 | Henderson | 156/648 |
| 5,345,213 | 9/1994 | Semancik et al. | 338/34 |

OTHER PUBLICATIONS

Jaeggi et al, "thermoelectric AC Power Sensor by CMOS Technology", *IEEE Electron Device Letters,* vol. 13, No. 7 (1992), p. 366.

Transaction of the Institute or Electrical Engineers of Japan, Part C. vol. 112–C, No. 12, 1 Dec. 1992 (Japan) pp. 763–768 T. Ogawa et al; *A Thin Film Gas Sensor Fabricated on a Diaphragm on a Silicon Substrate.*

Sensors and Actuators B, vol. B5, No. 1–4, 1991, Lausane, Switzerland, pp. 199–203 XP000239563; D. Keyvani et al, *A Planar Integrated Chlorinated Hydrocarbon Gas Sensor on a Silicon Substrate.*

Sensors and Actuators B, vol. B4, No. 3–4, 1 Jun. 1990, Switzerland pp. 533–538 XP000226170, M. Gall et al; *The Si Planar Sensor in Si Thin–Film Technology.*

5,464,966

MICRO-HOTPLATE DEVICES AND METHODS FOR THEIR FABRICATION

TECHNICAL FIELD

The present invention relates to silicon micromachining techniques and devices made thereby. In particular, the present invention relates to micro-hotplate devices and methods of fabricating the same.

BACKGROUND ART

The field of silicon micromachining has been researched for over 20 years. Although most of the recent media attention has focused on micro-motors and gears, other applications of silicon micromachining currently exist, including applications in sensor technologies.

Traditionally, silicon micromachined devices are manufactured in custom fabrication environments since the process steps for their fabrication significantly deviate from those for integrated circuits (IC's). In contrast to custom fabrication environments which are highly specific and extremely costly, IC's processed in silicon foundries offer the customer low cost and reliable custom parts. Many of these commercial foundries, also called Application Specific Integrated Circuit (ASIC) foundries, currently exist in the United States. These foundries are very reluctant to deviate from their standard processes to accommodate such things as silicon micromachined devices since they generally invested great amounts of time and money to optimize their processes for circuits. To date, no commercial ASIC foundry has made such a deviation.

The trend for silicon micromachined devices is moving in the direction of integration of mechanical elements with circuits. One example of this class of devices is "smart" sensors. Since the process of manufacturing sensors is significantly different from the IC process, the integration of circuits with sensors is a challenging problem. Recently, a technique was developed by Parameswaran (M. Parameswaran et al, "A New Approach for the Fabrication of Micromachined Structures", *Sensors and Actuators*, Vol. 19 (1989), pages 289–307) which allows for the fabrication of a class of micromechanical devices using chips that are commercially fabricated.

The inventors of the present invention have previously collaborated with Parameswaran (currently at Simon Fraser University in Vancouver) in the development of suspended heating elements to be used as micro-light sources for application as pixels in thermal displays (M. Parameswaran et al, "Micromachined Thermal Radiation Emitter from a Commercial CMOS Process", *IEEE Electron Device Letters*, Vol. 12, No. 2 (1991), pages 57–60). This collaborated work was based on CMOS compatible surface micromachining techniques.

While working on thermal displays, the present inventors envisioned that a similar type structure could be used to make a micro-hotplate device that had a polysilicon heating element (as in thermal display devices) and an aluminum plate to sense temperature and to distribute heat. Such a device could be easily integrated with circuitry for drive and control of the sensor and for communication with computers.

Similar ideas have been reported by Wang et al ("A Microfabricated Array of Multiple Thin Film Metal Oxide Sensors for Multicomponent Gas and Vapor Quantification", *Proceedings from the IEEE Solid State Sensors and Actuators Workshop*, Hilton Head, S.C. (1992), page 23), and Najafi et al ("An Integrated Multi-Element Ultra-Thin-Film Gas Analyzer", *Proceedings from the IEEE Solid State Sensors and Actuators Workshop*, Hilton Head, S.C. (1992), page 19). However, the methodologies for design and fabrication of these reported devices involve custom fabrication processes which limit the commercialization thereof. In addition, the components for the heating element and membrane are different from that of the present invention.

BRIEF SUMMARY OF THE INVENTION

It is accordingly one object of the present invention to provide a micro-hotplate structure which can be fabricated by conventional techniques which allow the manufacture of arrays of the micro-hotplate structures on a single substrate. It is a further object of the present invention to provide a micro-hotplate device which includes a conductive heat distribution plate which evenly distributes heat and means to sense the temperature of the device. A still further object of the present invention is to provide a micro-hotplate which includes means to measure electrical properties of materials which come into contact therewith. A still further object of the present invention is to provide for a method of fabricating the micro-hotplate devices which is based upon conventional techniques.

According to these and further objects of the present invention which will become apparent as the description thereof proceeds, the micro-hotplates of the present invention include a support substrate having a suspended microbridge structure formed thereon. A heating element is formed on the microbridge structure. The microbridge structure ensures that the heating element is thermally isolated from the support substrate. A conductive heat distribution plate is formed above the heating element. The conductive heat distribution plate is provided for evenly distributing heat from the heating element.

The present invention also provides an array of micro-hotplate devices.

The present invention further provides a method of making a micro-hotplate device. This method involves providing a support substrate having a first layer of an insulating material. Portions of the first layer of insulating material are identified as opening portions and a bridge portion. To fabricate the microbridge structure, the first layer of insulating material is removed from the opening portions and a portion of the substrate beneath the bridge portion is etched out through the opening portions so as to suspend and thermally isolate the bridge portion from the support substrate. Prior to etching, a heating element is formed on the bridge portion, a second layer of insulating material is formed on the heating element, a conductive heat distribution plate is formed on the second layer of insulating material, and a third layer of insulating material is formed on the conductive heat distribution plate.

BRIEF DESCRIPTION OF THE DRAWINGS

The present invention will hereafter be described with referenceto the annexed drawings which are given by way of non-limiting examples only in which.

BEST MODE FOR CARRYING OUT THE INVENTION

Figure 1A:
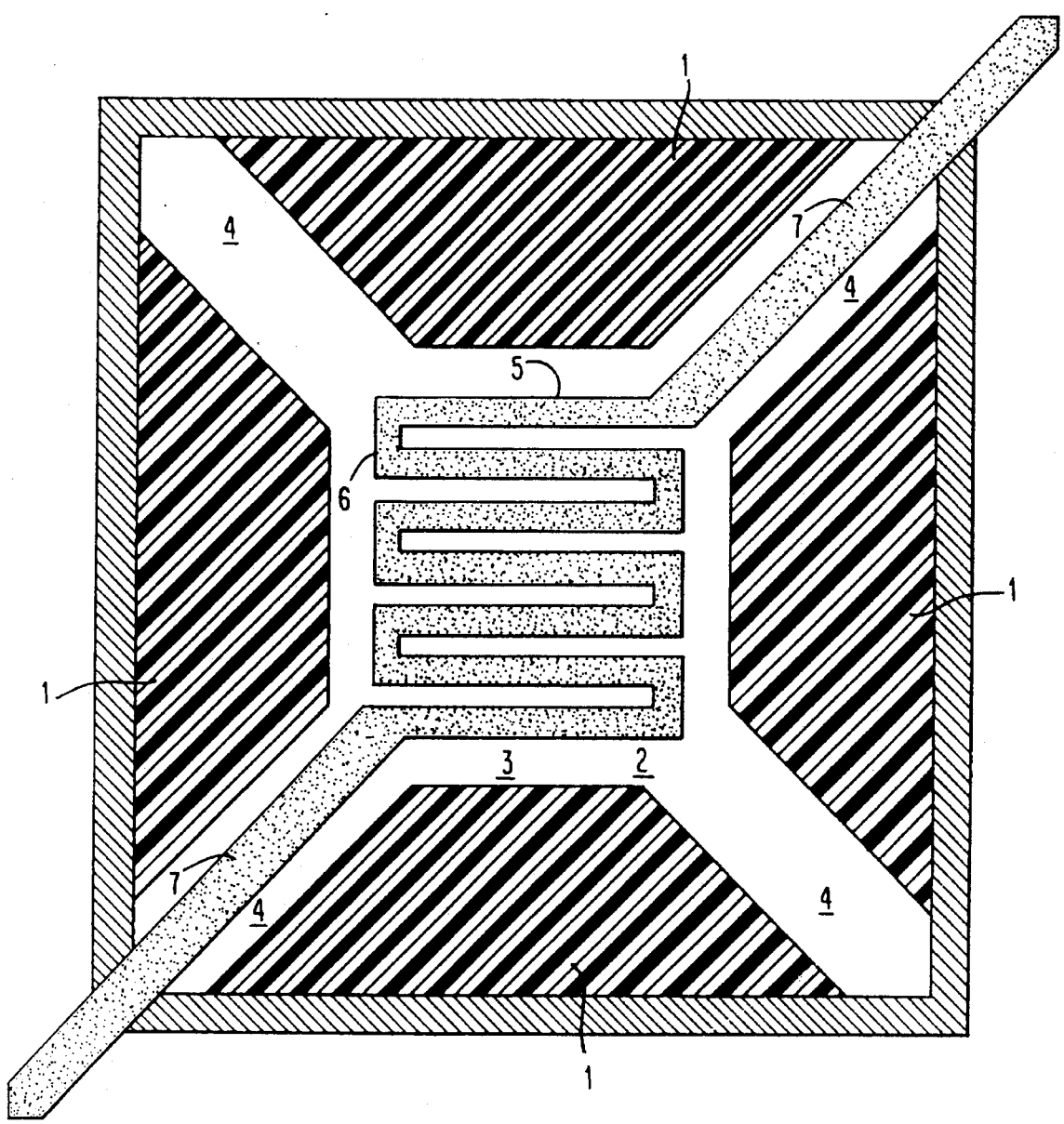
FIG. 1A is a schematic drawing showing the open areas and the heating element according to one embodiment of the present invention.

The present invention is directed to micro-hotplate devices which include a heating element that is thermally isolated on a suspended membrane or microbridge and a conductive heat distribution plate which is above and electrically isolated from the heating element. The conductive heat distribution plate includes electrical leads which allow for temperature sensing and control.

According to a further embodiment of the present invention, a plurality of conductive pads, e.g. four, are provided above the conductive heat distribution plate, and are electrically isolated therefrom by an intermediate layer of insulation material. Another electrical insulation layer is provided over the conductive pads, with openings therein which allow each of the conductive pads to be exposed to the external or ambient environment. The conductive pads are used to sense properties of materials which come into contact therewith.

The micro-hotplates of the present invention are fabricated using standard CMOS compatible micromachine processes. To form the suspended membrane of microbridge structure, a wafer or chip of silicon which includes a top layer of an insulation material such as silicon dioxide is provided with openings in the top layer of insulating material so as to expose portions of the underlying silicon surface. These openings can be designed and implemented without any additional masking at any CMOS foundry. If the openings are laid-out according to the present invention, a suspended membrane or microbridge with support legs will be formed in a post-fabrication etch process described below.

According to the present invention, standard CAD software used to design devices and circuits to be manufactured in integrated circuit processes are used to design the micro-hotplate(s) of the present invention. Therefore, large numbers of the micro-hotplates can be designed and fabricated on a single support substrate, i.e. wafer or chip, using conventional CMOS techniques.

There are a number of available software packages available which can be employed according to the present invention. One such software package which is available from the public domain and has been employed by the inventors during the course of the present invention is called MAGIC.

In order to use software packages such as MAGIC to design openings for the micromachining step, the technology file used in the software has to be modified. According to the modification, which is known and reported elsewhere (J. Marshall, M. Parameswaran, M. Zaghloul and M. Gaitan, "Methodology for the Computer-Aided Design of Silicon Micromachined Devices in a Standard CMOS Process", NISTIR, May 1992), a new layer, which in the present invention is referred to as "open" is formed. This layer is composed of IC fabrication masks that are available in standard CMOS processes but which are not normally used together, namely the glass cut, metal contacts, and poly and active area contacts. It is noted that while reference herein is made to the use of MAGIC, other CAD software packages could also be similarly modified in order to design the openings used in the present invention.

FIG. 1A shows the design of the openings and the heating element used according to one embodiment of the present invention. As shown in FIG. 1A, four openings 1 are provided along each side of the device of the present invention. The openings 1 expose the underlying silicon substrate, leaving a membrane or microbridge structure 2 which, after fabrication of the device is caused to be suspended by a post-fabrication etch process. The post-fabrication etch process forms an etch pit 18 (FIG. 5) beneath the membrane or microbridge 2. In a preferred embodiment, the membrane or microbridge 2 is formed of an insulation material such as glass, e.g. silica, which provides mechanical support for the suspended structure and electrical insulation. The final suspended nature of the membrane or microbridge 2 itself provides thermal insulation of the device.

In FIG. 1A, the membrane or microbridge 2 is depicted as having a square central portion 3 and four support legs 4 which extend from corners of the central portion 3 to the edge of the device. The choice of design layouts for the openings 1 and resulting membrane or microbridge 2 is not limited to that shown in FIG. 1A. Other design layouts could also be used as long as they result in a suspended membrane or microbridge 2. For example, more or less than four support legs could be used to support a central membrane or microbridge portion. In this regard, a cantilevered structure could be used a well as a rectangular membrane which is supported at opposite ends to the edge of the device.

The heating element 5 shown in FIG. 1A includes a serpentine ribbon portion 6 of a conductive material which has leads 7 at opposite ends thereof. The leads 7 extend over the support legs 4 as shown. The heating element 5 functions as a resistive heater when an electrical current is applied to the leads 7 thereof. The heating element 5 can be made of any conductive material including metals or metalloids or compounds thereof. However, a polysilicon heating element was found to be particularly suitable for purposes of the present invention.

In addition to functioning as a source of heat, the heating element 5 can also be used to sense temperature in a known manner. Thus, according to one embodiment of the present invention, the heating element 5 can be used as a resistive heater and as a temperature sensor. Accordingly to another embodiment of the invention, two separate, co-planar, parallel conductive lines are provided; one serving as a heater and the other serving as a temperature sensor.

Figure 1B:
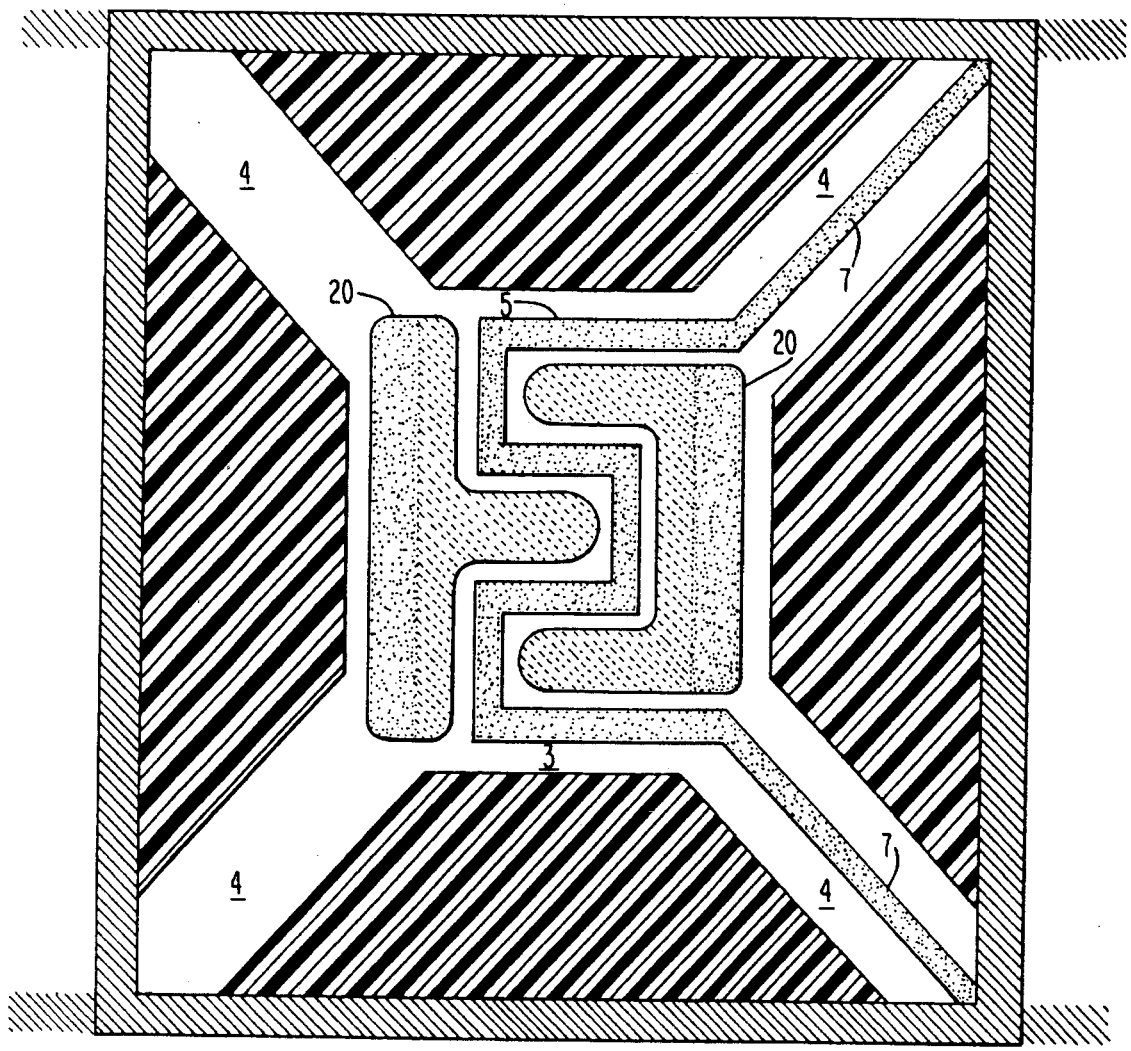
FIG. 1B is a schematic drawing showing an alternative/ embodiment of the heating element.

FIG. 1B is a schematic drawing showing an alternative embodiment of the heating element which includes adjacent, co-planar heat distribution elements or "islands". As depicted in FIG. 1B, the heating element 5 does not extend across the whole surface area of the central portion 3 of the membrane or microbridge 2. The surface area of the central portion 3 of the membrane or microbridge 2 which is not covered by the heating element 5 is provided with islands 20 of heat conducting material which are co-planar with the heating element 5. The material from which the heat conducting islands 20 are made can be the same or different from the material from which the heating element 5 is made. For example, both the heating element 5 and the heat conducting islands 20 can be made from polysilicon, which is thermally more conducting than silicon dioxide. The heat conducting islands 20 need not be connected to electrical leads. The heat conducting islands 20 can also be used in conjunction with the co-planar temperature sensor discussed above.

For convenience, all the materials used in the device of the present invention should be selected from those available from, or compatible with, standard CMOS processes. Commercial CMOS processes can be employed which can provide layers of polysilicon and aluminum; these processes can be used in known manners to fabricate the contacts, heaters, and temperature sensors used in the device of the present invention.

Figure 2:
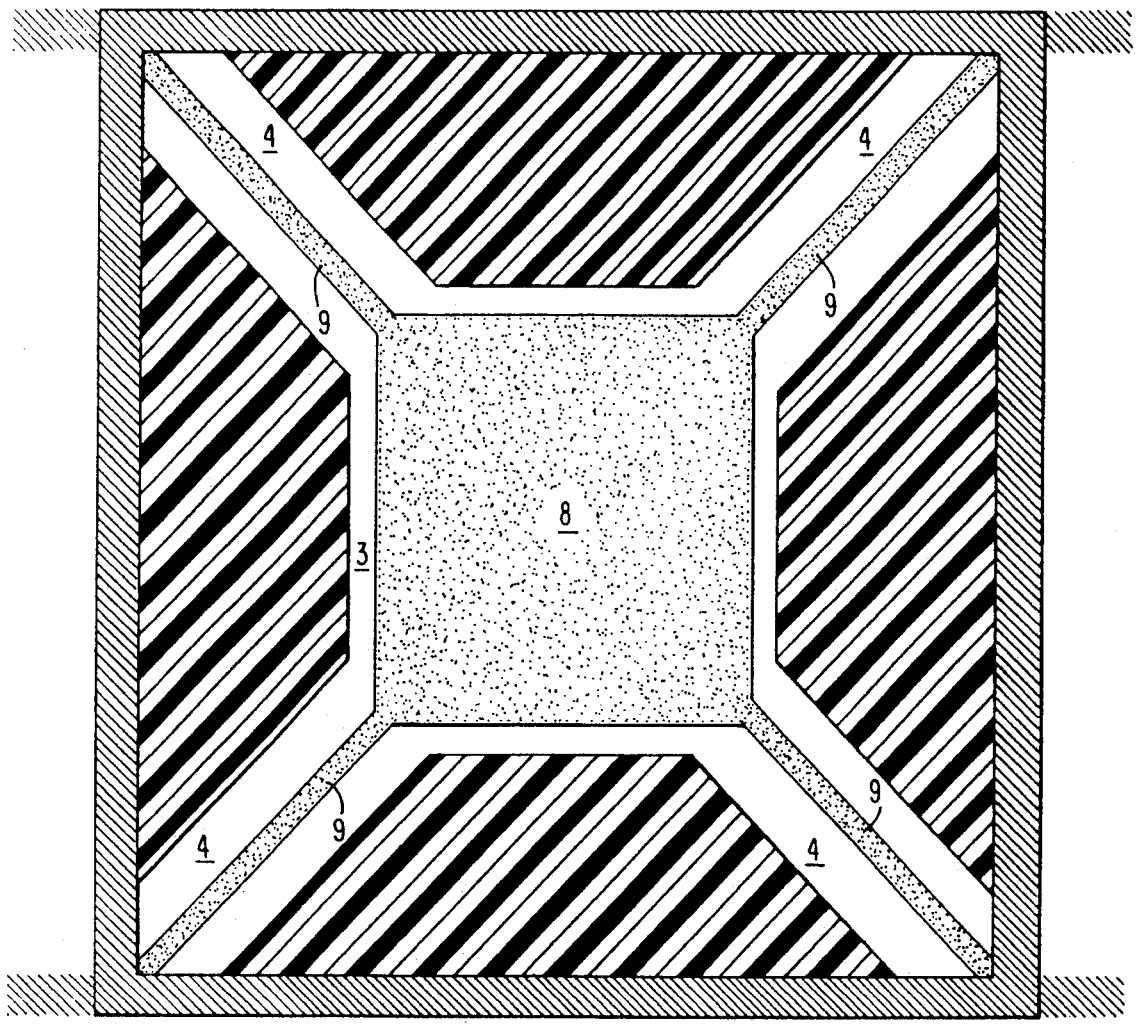
FIG. 2 is a schematic drawing showing the conductive heat distribution plate with four point contacts according to one embodiment of the present invention.

FIG. 2 shows the conductive heat distribution plate used in the micro-hotplate according to one embodiment of the present invention. The conductive heat distribution plate 8 is provided on top of the central portion 3 of the membrane or microbridge 2 and has a surface area which is preferably coextensive and aligned with the central portion 3 of the membrane or microbridge 3, or at least coextensive and aligned with the heating element 5, absent the leads thereof. The conductive heat distribution plate 8 and membrane or microbridge 2 are separated by a layer of insulating material 13 (FIG. 5) such as glass, e.g., silica, which provides electrical insulation therebetween. One of four leads 9 extend from each corner of the conductive heat distribution plate 8 on the support legs 4 as shown. These leads 9 allow for temperature sensing by measuring resistivity of the metallic heat distribution plate 8. In this regard, two of the leads are used for voltage sensing and the other two leads are used as current source lines in a conventional manner.

The conductive heat distribution plate 8 functions both to evenly distribute heat from the heating element 5 to the top surface of the micro-hotplate and as a means to sense temperature near the top surface of the device. In this regard, the temperature is sensed by measuring the change in resistivity of the material from which the conductive heat distribution plate 8 is made as a function of temperature. This resistivity change is characterized by a term called the temperature coefficient of resistance, (TCR) and can be determined by measurements using an external hot plate as a reference in a conventional manner. The conductive heat distribution plate 8 can be made from any metal or metalloid or compounds thereof which conducts heat and can withstand temperatures at which the device is to be used. For purposes of the present invention aluminum was found to be a suitable material from which to make the conductive heat distribution plate 8. However, the conductive heat distribution plate 8 could be made from conductive materials having higher melting temperatures if the device is to be operated at high temperatures.

If heat dispersal without temperature sensing is desired from the conductive heat distribution plate 8, the leads 9 can be omitted. This would simplify the structure and improve thermal isolation by limiting conductive paths to and from the device.

Figure 3:
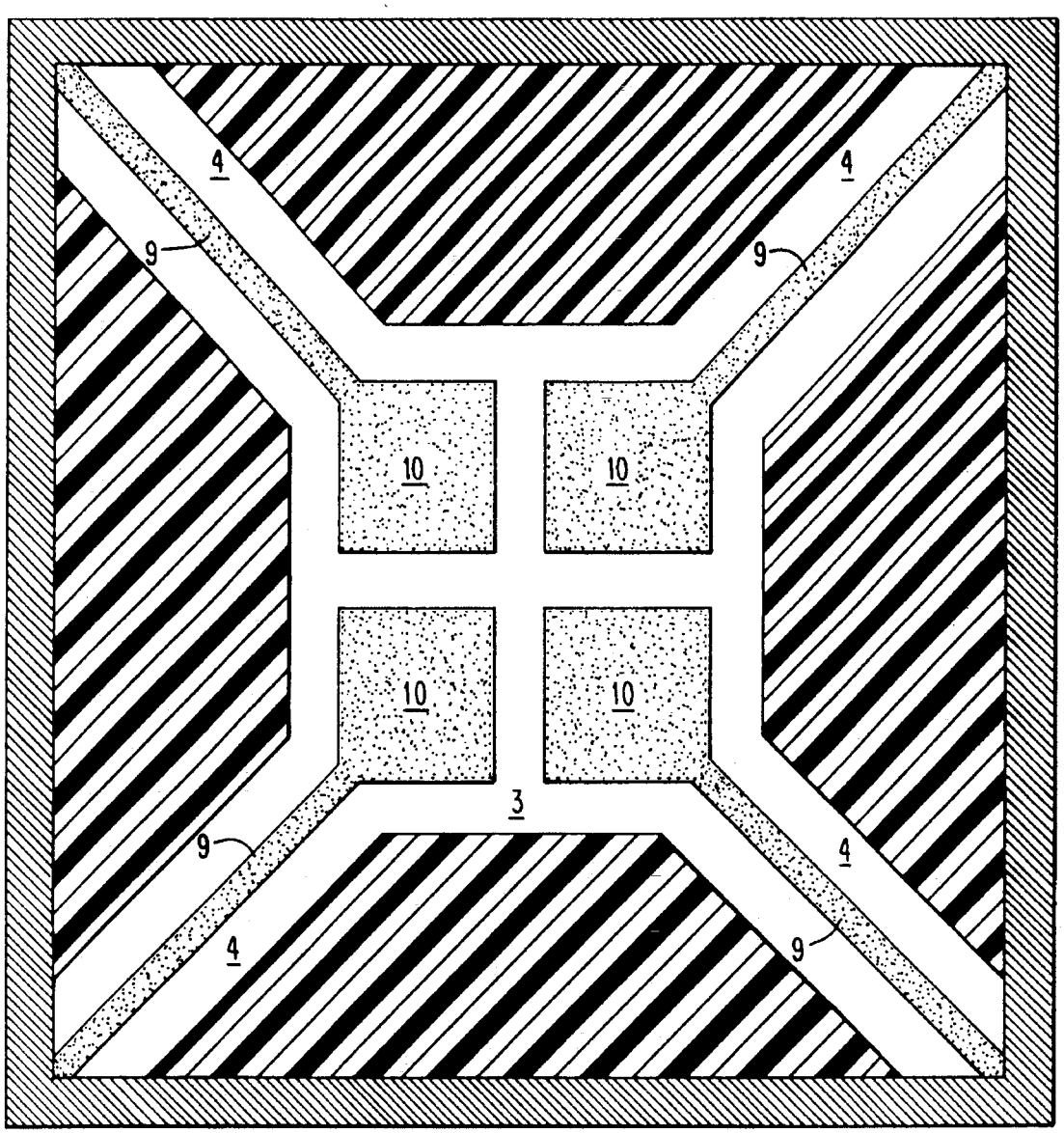
FIG. 3 is a schematic drawing of the contact pads according to one embodiment of the present invention.

FIG. 3 shows the contact pads that are exposed to the external or ambient environment to which the device is exposed. As shown in FIG. 3 the contact pads 10 are symmetrically arranged over the conductive heat distribution plate 8. An electrical insulating layer 14 (FIG. 5) such as a glass, e.g., silica, is provided between the contact pads 10 and the conductive heat distribution plate 8. The contact pads 10 are covered by another layer 15 (FIG. 5) of an electrical insulating material such as glass, e.g., silica, which includes a like number of openings 16 (FIG. 5) that allow each of the contact pads 10 to be exposed to the external or ambient environment.

In operation, as discussed below, the contact pads 10, which are made form a conductive material such as metals or metalloids or compounds thereof, are used as point contacts to measure the resistance of materials, i.e., solids, liquids or gas which come into contact with, or are formed on, the contact pads 10 on the top of the device. For this purpose, conductive leads 11 extend from each of the contact pads 10 on the support legs 4 as shown.

Figure 4:
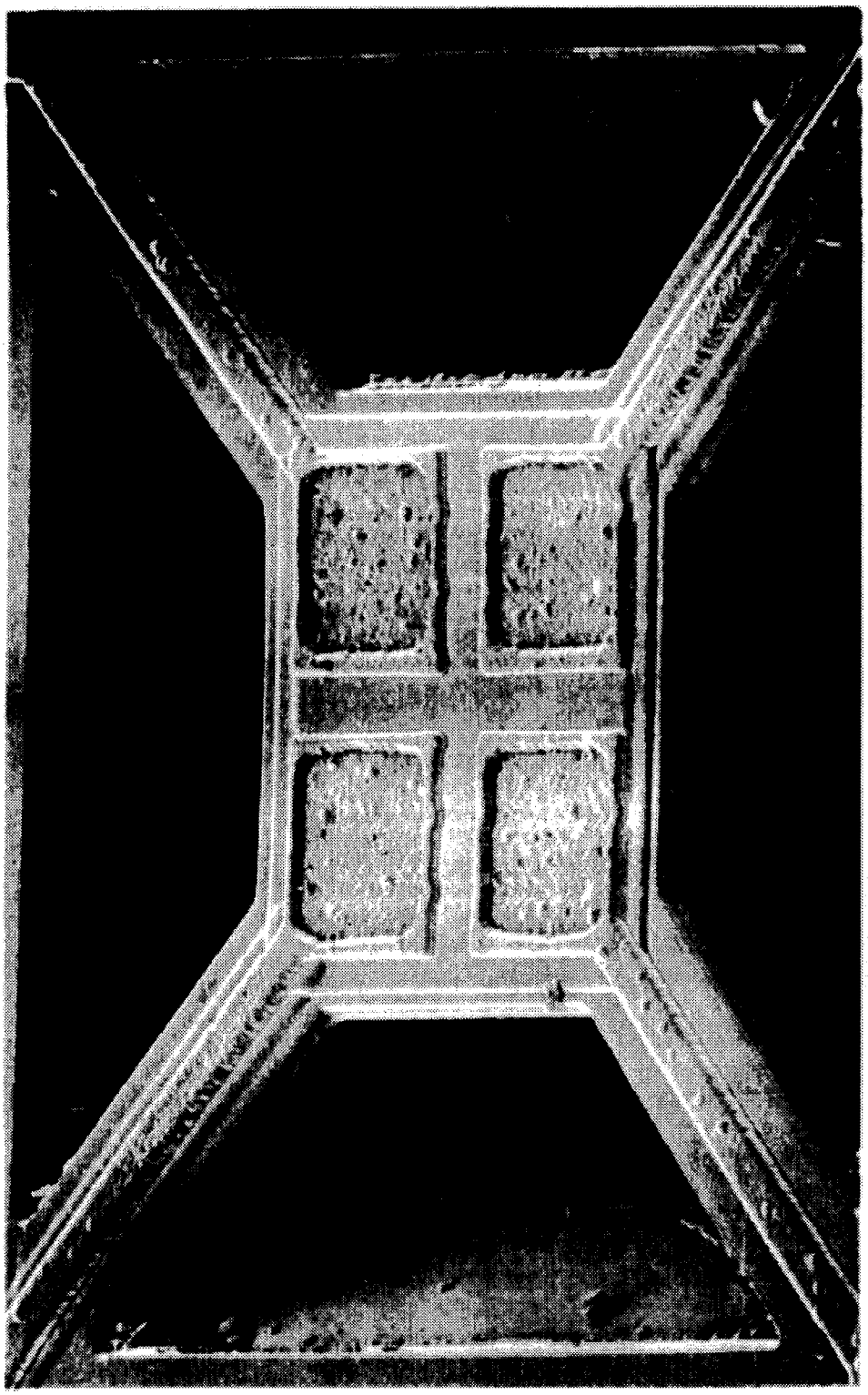
FIG. 4 is a scanning electron microscope micrograph (SEM) of the micro-hotplate of FIGS. 1–3.

FIG. 4 is a scanning electron microscope micrograph (SEM) of the micro-hotplate of FIGS. 1–3. The structure of this single device is the same as the four-array device discussed below with reference to FIG. 5 below.

Figure 5:
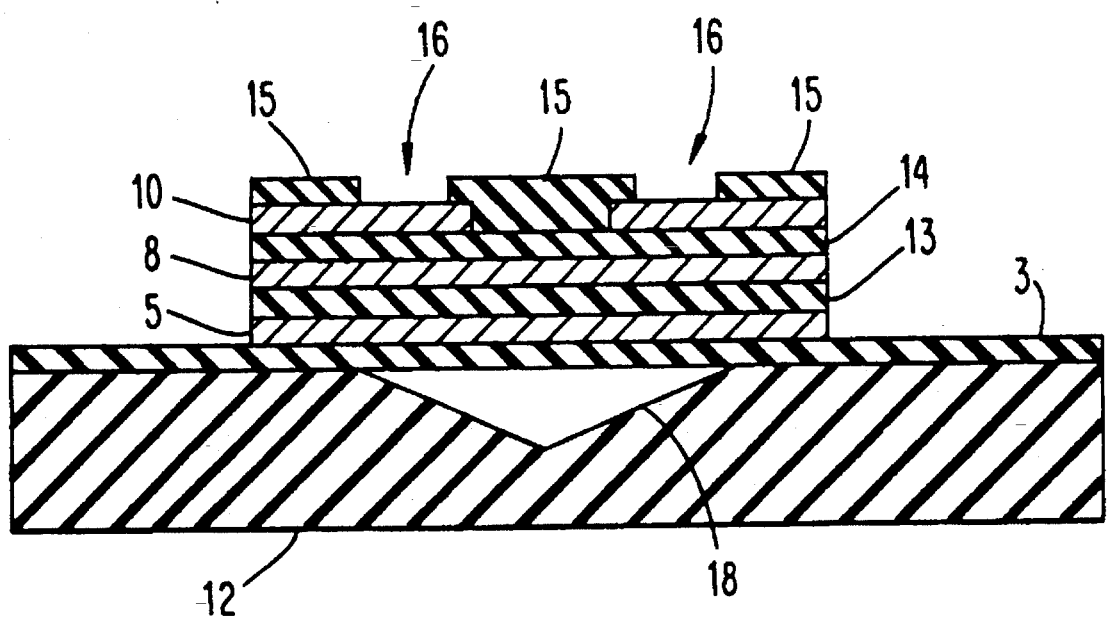
FIG. 5 is a schematic cross-sectional view of the micro-hotplate according to one embodiment of the present invention.

FIG. 5 is a schematic cross-sectional view of the micro-hotplate according to one embodiment of the present invention. As depicted in FIG. 5, according to a preferred embodiment, each micro-hotplate device has a suspended membrane or microbridge together with layers of polycrystalline silicon (PXS), silicon dioxide ($SiO_2$), and aluminum (Al). These preferred materials are compatible with the CMOS processes used to fabricate the devices on the chip. The layer sequence on the silicon chip 12 from bottom to top as shown includes the suspended membrane or microbridge 3 which is made of silicon dioxide, the heating element 5 which is made of polycrystalline silicon, an insulating layer 13 of silicon dioxide, the conductive heat distribution plate 8 which is made of aluminum, another insulating layer 14 of silicon dioxide, four contact pads 10 which are made of aluminum, and a final insulating layer 15 of silicon dioxide with four openings 16 therein which communicate with the contact pads in the layer below.

Figure 6:
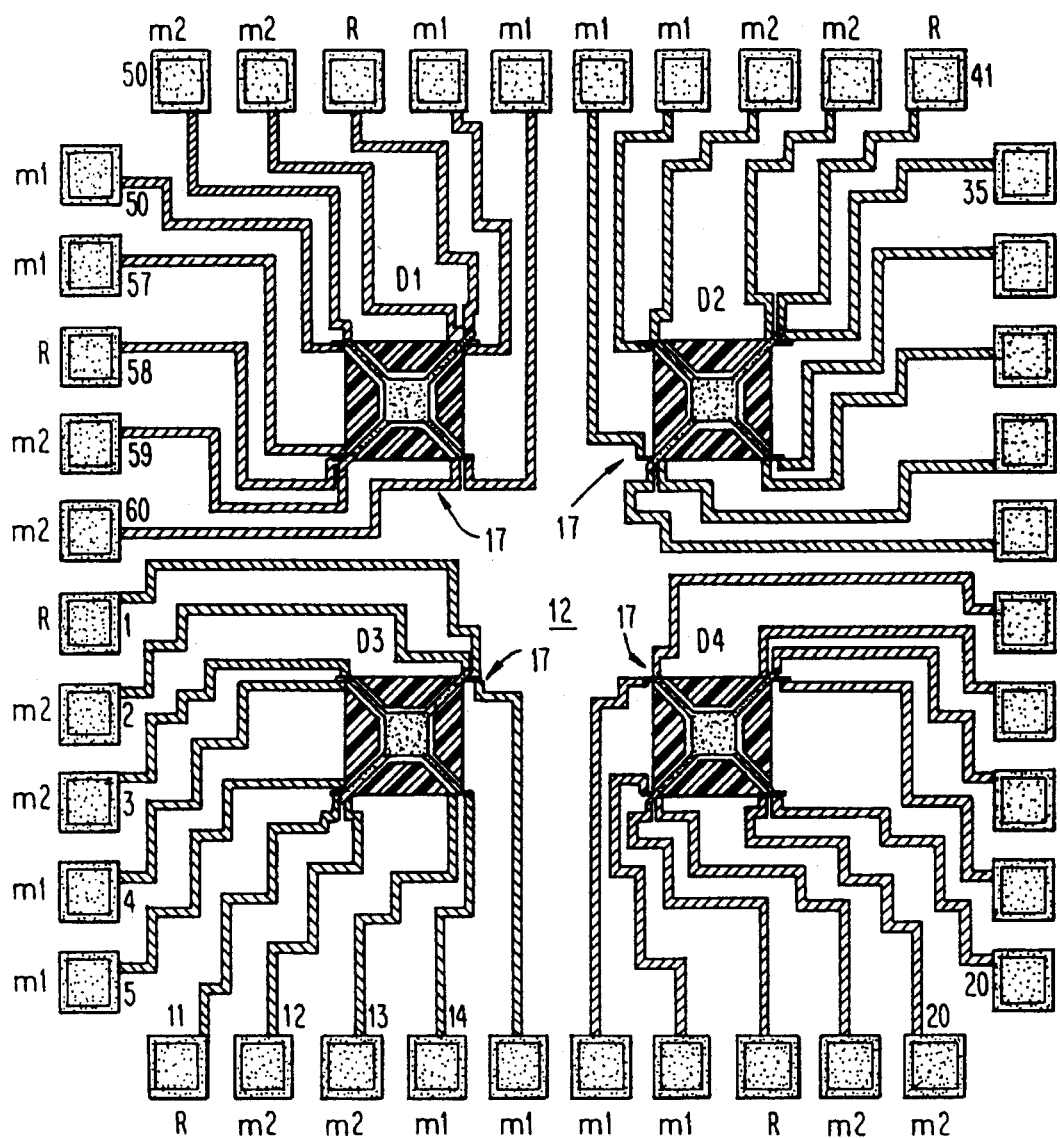
FIG. 6 is a schematic drawing of an array of four micro-hotplates according to the present invention.

FIG. 6 shows an array of four micro-hot plates on a single substrate according to the present invention. As shown in FIG. 6, the array includes a substrate support, e.g., a silicon chip, with an array of four micro-hotplates 17 with 10 leads per device. It is noted that while four micro-hotplates are shown in the array of FIG. 6, it is a simple matter to use the same technology to produce hundreds of similar devices on a single support substrate, i.e., a wafer or chip.

In operation, a suitable current of up to about 20 mA, and more typically about 4 mA is applied to the leads 7 of the heating element 5. In response, the device heats up to a temperature related to the current. Temperature is measured by supplying a suitable current of up to about 50 mA, and more typically 10 mA, to two of the four leads 9 of the conductive heat distribution plate 8 and measuring the voltage drop, which is generally up to about 10 mV, and more typically about 1 mV, across the other two leads of the conductive heat distribution plate 8.

The device depicted in FIG. 5 and discussed above, has a operable temperature range of from ambient temperature (normally room temperature, although the chip may be mounted on a cold surface to obtain lower temperatures) to about 600° C. Above 600° C., aluminum begins to deform (by electromigration, etc.) and eventually melt. The device can be easily designed to operate at higher temperatures, e.g., greater than 1000° C. by replacing the aluminum elements with polysilicon. For materials science studies at high temperatures in oxidizing environments, one may use a top layer of Pt to serve as a platinum resistance thermometer. Thin film thermocouple elements may also be included to measure temperature in some applications.

Foundry processes that use metals other than aluminum, e.g., tungsten, will allow other metals to be used in the devices of the present invention and will provide micro-hotplates than can operate at much higher temperatures.

For clarity, the wire connections to each of the leads of the micro-hotplates has not been shown. However, in use, the chip supporting one or more micro-hotplates is mounted on a ceramic chip carrier, having conventional connections between the chip and carrier leads accomplished using gold wirebonds.

The size of the initial micro-hotplate that was designed was 200 micrometers on a side. However this initial size is certainly not limiting since it is clear that other sizes could be chosen. In this regard, the present inventors have successfully designed and fabricated similar layouts to produce devices in a range of 50 micrometers to 800 micrometers.

No limitations have yet been encountered which limit the large end size at which a device can be made. However, small devices less than 50 micrometers may not be desirable since good thermal isolation may not be achieved.

Once the device is designed using CAD software, the file can be saved for future use. Since the devices of the present invention are manufactured using standard CMOS processes, conventional circuits can be added for temperature control and sensing and communication according to known techniques. It is noted that other silicon foundry processes are available such as BICMOS, BIPOLAR, etc. and that this methodology is also compatible with those processes.

While the device of the present invention is designed by making use of standard CMOS compatible micromachine processes, CMOS foundries do not currently offer the additional post-fabrication etching step required to form the suspended membrane or microbridge structure of the present invention. Therefore, this step is carried out after the CMOS fabrication process. This method of providing suspended membranes or microbridges has been shown to provide good thermal isolation in other devices (M. Parameswaran et al, "Micromachined Thermal Radiation Emitter from a Commercial CMOS Process", *IEEE Electron Device Letters*, Vol. 12, No. 2 (1991), pages 57–60).

After the designs are fabricated, the completed chips are subjected to a post-fabrication etch procedure to complete the fabrication of the device. In the post-fabrication etch a mixture of ethylenediamine-pyrocatechol-water-pyrazin (EDP, Transene Company) is utilized to form an etch pit 18 (FIG. 6) beneath at least the central portion 3 of the membrane or microbridge 2. EDP can be mixed in-house as reported in the literature (Jaeggi et al, "Thermoelectric AC Power Sensor by CMOS Technology", *IEEE Electron Device Letters*, Vol. 13, No. 7 (1992), page 366).

In the post-fabrication etch procedure used in the present invention aluminum hydroxide (AlOH) was added to the EDP in order to limit the attack of the EDP on exposed aluminum surfaces. The mixture was heated in a reflux container to 97° C. and the devices were etched for approximately 1 hour 15 minutes. After this step the fabrication is complete and the devices can be packaged and tested.

According to one embodiment, electroplating and electroless plating have been utilized to deposit barrier materials such as nickel and copper on exposed aluminum contact pads and on exposed silicon regions in order to protect these layers from the echant and to increase the operable temperature range of the device. This plating can be performed selectively on the contact pads, or the exposed silicon regions, or both utilizing maskless deposition techniques.

Thermal isolation which is provided for by the etching beneath the membrane or microbridge is necessary in order to heat the surface to elevated temperatures (in the range of ambient to over 1000° C.) at power levels that are compatible with IC-based applications (less than 100 mW per heater).

Thermal response time and power requirements of the device may be controlled by limiting or increasing the number and size of the legs 4 and the various electrical leads on the legs. In general, higher thermal conducting paths (more and/or shorter legs and more and/or larger electrical leads) will provide a faster response time (on the order of one microsecond or less) at a higher power requirement. Fewer legs and less electrical leads will provide a lower power requirement, but a slower response time.

Devices have been fabricated which have a response time of about 1 millisecond and require 10 mW of power to attain a temperature of 500° C.

The present inventors are not aware of any other methodologies which can be used to manufacture micro-hotplates with monolithic circuits using conventional foundry processes. Accordingly, the device of the present invention has advantages over other similar known devices in that it can be manufactured using commercial foundries and does not require any additional masking steps for the post-fabrication step. Other devices that may be similar are fabricated in accordance with custom processes which utilize materials layers that are different and not compatible with commercial foundry processes. Moreover, suspended membranes are created by etching from the back side of the wafer or chip utilizing additional masking steps. By being able to fabricate the devices of the present invention in a commercial foundry environment, the devices have the advantages of lower cost, fast fabrication, easy customization, fast technology transfer, and VLSI circuit compatibility.

The micro-hotplate devices of the present invention can be utilized to heat materials, while sensing electrical properties of the materials. Moreover, it is possible to deposit interactive material layers on the micro-hotplates, for use in environmental sensing such as gas sensing in exhaust emissions, in-situ process control where a material can be processed locally at some desired temperature, and process monitoring. For environmental sensing, such as gas sensing, an additional material layer can be deposited on the micro-hotplate and the temperature of this material can then be controlled with the monolithic electronics such as temperature controller and computer interface. For process monitoring application, the devices of the present invention can be used, for example, as a way of sensing the resistivity of a material as it is deposited and adjusting the temperature of the micro-hotplate(s) to compensate for errors in real time. Other uses for the micro-hotplates will be apparent to those skilled in the art.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A micro-hotplate device which comprises:
   a support substrate;
   a microbridge structure formed on said support substrate, said microbridge structure having a suspended portion;

a heating element formed directly on said microbridge structure so as to be thermally isolated from said support substrate;

a layer of electrically insulating material formed directly on said heating element; and a conductive heat distribution plate formed directly on said layer of electrically insulating material, said conductive heat distribution plate being centrally located over said microbridge structure.

2. A micro-hotplate according to claim 1, wherein said conductive heat distribution plate includes four leads for sensing temperature.

3. A micro-hotplate according to claim 1, wherein the microbridge structure comprises a layer of electrical insulation material.

4. A micro-hotplate according to claim 3, wherein a central portion of the microbridge structure is suspended over an etch pit which is formed in the substrate support.

5. A micro-hotplate according to claim 4, wherein said etch pit is formed with a closed bottom.

6. A micro-hotplate according to claim 3, wherein a central portion of the microbridge structure is suspended over an etch pit which has a closed bottom.

7. A micro-hotplate according to claim 1, further comprising a layer of an electrical insulating material formed on a side of the conductive heat distribution plate which side is opposite to a side thereof which faces said heating element.

8. A micro-hotplate according to claim 7, further comprising a plurality of contact pads which are formed on said layer of electrical insulating material.

9. A micro-hotplate according to claim 8, wherein said contact pads are covered with another layer of an electrical insulating material which includes through holes that allow portions of the contact pads to be exposed through said another layer of electrical insulating material.

10. A micro-hotplate according to claim 8, wherein said contact pads include electrical leads.

11. A micro-hotplate according to claim 8, wherein said contact pads comprise aluminum.

12. A micro-hotplate according to claim 1, wherein said micro-hotplate has a size of between about $2.5 \times 10^3$ and $6.4 \times 10^5$ square microns.

13. A micro-hotplate according to claim 1, wherein said support substrate comprises silicon.

14. A micro-hotplate according to claim 13, wherein said silicon support substrate comprises a silicon wafer or chip.

15. A micro-hotplate according to claim 1, wherein said heating element comprises polysilicon.

16. A micro-hotplate according to claim 1, wherein said conductive heat distribution plate comprises aluminum.

17. An array of micro-hotplate devices which comprises:

a support substrate;

a plurality of microbridge structures formed on said support substrate, each of said plurality of microbridge structures having a suspended portion;

individual heating elements formed directly on each of said plurality of microbridge structures so as to be thermally isolated from said support substrate;

a layer of electrically insulating material formed directly on each of said heating elements; and individual conductive heat distribution plates formed directly on said layer of electrically insulating material above each heating element and located centrally over an underlying microbridge structure.

18. A method of making a micro-hotplate device which comprises:

providing a support substrate having a first layer of an insulating material;

designing said first layer of insulating material into opening portions and a bridge portion;

removing the first layer of insulating material from said opening portions;

forming a heating element directly on said bridge portion;

forming a second layer of insulating material directly on said heating element;

forming a conductive heat distribution plate directly on said second layer of insulating material, said conductive heat distribution plate being located centrally over said microbridge structure;

forming a third layer of insulating material on said conductive heat distribution plate; and thereafter, etching out a portion of said support substrate beneath said bridge portion through said opening portions so as to suspend and thermally isolate said bridge portion from said support substrate.

19. A method of making a micro-hotplate device according to claim 18, further comprising forming four leads which are connected to said conductive heat distribution plate.

20. A method of making a micro-hotplate device according to claim 18, further comprising, prior to said etching step, forming a plurality of contact pads on said third layer of insulating material; and forming a fourth layer of insulating material on said contact pads, with through holes therein which allow portions of said contact pads to be exposed through said fourth layer of insulating material.

21. A micro-hotplate device which comprises:

a support substrate;

a microbridge structure formed on said support substrate;

a heating element formed on said microbridge structure so as to be thermally isolated from said support substrate; and a conductive heat distribution plate formed above said heating element, said micro-hotplate made by:

providing a first layer of an insulating material on said support substrate;

dividing said first layer of insulating material into opening portions and a bridge portion;

removing the first layer of insulating material from said opening portions;

forming said heating element directly on said bridge portion of said first layer of insulating material;

forming a second layer of insulating material directly on said heating element;

forming said conductive heat distribution plate directly on said second layer of insulating material, said conductive heat distribution plate being located centrally over said bridge portion;

forming a third layer of insulating material on said conductive heat distribution plate; and thereafter, etching out a portion of said support substrate beneath said bridge portion through said opening portions so as to suspend and thermally isolate said bridge portion from said support substrate.

22. A micro-hotplate according to claim 21, wherein said conductive heat distribution plate includes four leads for sensing temperature.

23. A micro-hotplate according to claim 21, further comprising a plurality of contact pads which are formed on said third layer of insulating material.

24. A micro-hotplate according to claim 23, wherein said contact pads are covered with another layer of an electrical insulating material which includes through holes that allow portions of the contact pads to be exposed through said another layer of electrical insulating material.

25. A micro-hotplate according to claim 23, wherein said contact pads include electrical leads.

26. A micro-hotplate according to claim 23, wherein said contact pads comprise aluminum.

27. A micro-hotplate according to claim 21, wherein said micro-hotplate has a size of between about $2.5 \times 10^3$ and $6.4 \times 10^5$ square microns.

28. A micro-hotplate according to claim 21, wherein said support substrate comprises silicon.

29. A micro-hotplate according to claim 28, wherein said silicon support substrate comprises a silicon wafer or chip.

30. A micro-hotplate according to claim 21, wherein said heating element comprises polysilicon.

31. A micro-hotplate according to claim 21, wherein said conductive heat distribution plate comprises aluminum.

* * * * *